United States Patent
Schouenborg et al.

(10) Patent No.: US 12,023,210 B2
(45) Date of Patent: Jul. 2, 2024

(54) METHOD OF MICROELECTRODE IDENTIFICATION

(71) Applicant: NEURONANO AB, Karlshamn (SE)

(72) Inventors: Jens Schouenborg, Lund (SE); Jonas Thelin, Lund (SE); Mohsin Mohammed, Lund (SE)

( * ) Notice: Subject to any disclaimer, the term of this patent is extended or adjusted under 35 U.S.C. 154(b) by 872 days.

(21) Appl. No.: 16/617,152

(22) PCT Filed: May 29, 2018

(86) PCT No.: PCT/SE2018/000014
§ 371 (c)(1),
(2) Date: Nov. 26, 2019

(87) PCT Pub. No.: WO2018/222101
PCT Pub. Date: Dec. 6, 2018

(65) Prior Publication Data
US 2020/0129266 A1    Apr. 30, 2020

(30) Foreign Application Priority Data

May 29, 2017   (SE) .................................. 1700109-0

(51) Int. Cl.
| | |
|---|---|
| A61B 6/12 | (2006.01) |
| A61B 5/24 | (2021.01) |
| A61B 90/00 | (2016.01) |
| A61B 90/90 | (2016.01) |

(Continued)

(52) U.S. Cl.
CPC ................ *A61B 90/90* (2016.02); *A61B 5/24* (2021.01); *A61B 6/12* (2013.01); *A61B 90/39* (2016.02);

(Continued)

(58) Field of Classification Search
CPC . A61B 90/90; A61B 90/39; A61B 2090/3966; A61B 5/24; A61B 2090/376;

(Continued)

(56) References Cited

U.S. PATENT DOCUMENTS

| 4,903,702 A | 2/1990 | Putz .............................. 128/642 |
| 8,118,803 B1 | 2/2012 | Chow ........................... 604/524 |

(Continued)

FOREIGN PATENT DOCUMENTS

| EP | 1 970 019 A1 | 9/2008 |
| EP | 2 612 691 A1 | 7/2013 |
| WO | WO 2009/075625 A1 | 6/2009 |

OTHER PUBLICATIONS

International Search Report dated Aug. 29, 2018 in corresponding PCT International Application No. PCT/SE2018/000014.
Written Opinion dated Aug. 29, 2018 in corresponding PCT International Application No. PCT/SE2018/000014.

*Primary Examiner* — Colin T. Sakamoto
(74) *Attorney, Agent, or Firm* — OSTROLENK FABER LLP

(57) ABSTRACT

A method of identifying upon insertion into soft tissue a microelectrode of a set of three or more microelectrodes each comprising an electrically conductive body comprises providing the microelectrode with a unique metallic pattern of three or more sections separated from each other and disposed in an axial direction on the body and/or on one or more insulating layers on the body; inserting the microelectrode into the tissue simultaneously or consecutively with the other microelectrodes of the set; detecting the pattern by computer tomography (CT) or X-ray. Also disclosed are microelectrodes provided with unique patterns and sets of such microelectrodes and their use.

21 Claims, 3 Drawing Sheets

(51) Int. Cl.
*A61B 90/94* (2016.01)
*A61N 1/05* (2006.01)
*A61B 6/03* (2006.01)

(52) U.S. Cl.
CPC ............... *A61B 90/94* (2016.02); *A61N 1/05* (2013.01); *A61B 6/032* (2013.01); *A61B 2090/376* (2016.02); *A61B 2090/3966* (2016.02); *A61B 2562/0209* (2013.01)

(58) Field of Classification Search
CPC ... A61B 90/94; A61B 2562/0209; A61B 6/12; A61B 6/032; A61L 27/04; A61N 1/05; A61N 5/05–0575
See application file for complete search history.

(56) References Cited

U.S. PATENT DOCUMENTS

| | | | |
|---|---|---|---|
| 8,386,006 B2* | 2/2013 | Schouenborg | A61N 1/0551 600/377 |
| 8,788,064 B2* | 7/2014 | Mercanzini | A61B 17/34 607/45 |
| 9,622,676 B2* | 4/2017 | Masmanidis | A61N 1/0529 |
| 2005/0065586 A1* | 3/2005 | Johnson | A61B 5/287 607/122 |
| 2005/0171587 A1 | 8/2005 | Daglow et al. | 607/116 |
| 2012/0271248 A1 | 10/2012 | Nesbitt et al. | 604/265 |
| 2017/0143966 A1* | 5/2017 | Reymers | A61N 7/00 |

* cited by examiner

METHOD OF MICROELECTRODE IDENTIFICATION

CROSS-REFERENCE TO RELATED APPLICATIONS

The present application is a 35 U.S.C. §§ 371 national phase conversion of PCT/SE2018/000014, filed May 29, 2018, which claims priority to Swedish Patent Application No. 1700109-0, filed May 29, 2017, the contents of which are incorporated herein by reference. The PCT International Application was published in the English language.

FIELD OF THE INVENTION

The present invention relates to a method of identifying the disposition of a particular microelectrode amongst a number of microelectrodes of same design implanted in soft tissue and to individually marked microelectrodes for use in the invention.

BACKGROUND OF THE INVENTION

The implantation into soft tissue, such a nervous or endocrine tissue, of more than one microelectrode at a time is well known. For instance, at least three and preferably at least four microelectrodes are required for spatial identification of a neuron by monitoring the electrical signals originating from the neuron. A requirement for such monitoring is information about the spatial disposition of the microelectrodes in the tissue. In a situation when multiple microelectrodes are spread out in the tissue for stimulation of excitable cells information about their spatial disposition is required for identification of the cells or groups of cells being stimulated by each electrode. Provided that the spatial disposition of the implanted microelectrodes is known a more efficient stimulation procedure can be designed by combining magnetic resonance imaging (MRI) and knowledge about which structures are capable of producing therapeutic effect on stimulation.

For implantation of two or more microelectrodes at the same time the microelectrodes are bundled by a permanent or temporary means. When bundled by a temporary means the identification of the disposition of a particular microelectrode in the tissue upon its release from the bundling means is problematic, in particular with microelectrodes of identical or substantially identical shape or with microelectrodes that adopt an identical or substantially identical shape during implantation.

OBJECTS OF THE INVENTION

A primary object of the present invention is to provide a method of identifying a particular microelectrode inserted into soft tissue of a person or animal amongst a number of microelectrodes of same design or substantially same design.

Another object of the invention is to provide a microelectrode for use in the method.

Further objects will become evident from the following summary of the invention, a number of preferred embodiments thereof illustrated in a drawing, and the appended claims.

SUMMARY OF THE INVENTION

According to the present invention is provided a method of identifying, by radiative means, of a microelectrode comprised by a set of two or more microelectrodes of a design that does not allow their identification by radiative means, in particular of same or similar design implanted in soft tissue, in particular nervous or endocrine tissue. Identification comprises identifying a particular microelectrode in a set of implanted microelectrodes, that is, in respect other microelectrodes of the set, but also in respect of its disposition in the tissue. An electrode of a diameter of up to 100 µm, in particular of up to 50 µm is considered to qualify as a microelectrode.

The method of the invention comprises providing two or more microelectrodes of same design or of a design that does not allow their identification by radiative means, which are desired to be individually identified upon insertion into soft tissue. In particular, it is desired for a microelectrode to be identifiable both individually and in respect of the position of a distal section thereof providing electrical contact with surrounding tissue. The contact providing distal section can be a section extending from the distal end or disposed in proximity of the distal end of the microelectrode. According to one preferred aspect of the invention a microelectrode of the invention is one that is inserted into soft tissue simultaneously with other microelectrodes in form of a bundle or array, that is, in a fixed spatial relationship with them, but which loses the fixed spatial relationship upon degradation by dissolution or degradation or both of the means providing the fixed relationship. According to another preferred aspect of the invention a microelectrode of the invention is one that is inserted into soft tissue consecutively with other microelectrodes or is inserted into soft tissue simultaneously with one or more microelectrodes and consecutively in respect of one or more microelectrodes.

An identifiable microelectrode of the invention comprises an electrically conducting oblong electrode body partially covered by a first insulation layer of polymer extending from the proximal end thereof, a unique pattern comprising a metal or metal alloy disposed on a distal portion of the insulation layer, a second insulation layer disposed on the pattern. For insertion into soft tissue the two or more identifiable microelectrodes are comprised by a microelectrode bundle or array disposed in a matrix of a material dissolvable and/or swellable in aqueous body fluid. To facilitate insertion the matrix can be provided with a coat with glidant properties when hydrated, such as a coat of dry gelatin or hyaluronic acid. The microelectrode body is preferably cylindrical. The microelectrode body is electrically conducting and consists or comprises a metal, in particular a noble metal and/or an electrically conducting polymer.

Upon insertion of the bundle or array into the tissue the matrix material is dissolved or swells by contact with aqueous body fluid. The position of the portion of the microelectrode carrying the pattern is thereupon determined by radiative means, in particular by computer tomography (CT) but also by X-ray. Since the geometry of a microelectrode of the invention is known the determination of the position of the pattern also allows determination of neighbouring portions of the microelectrode with good precision. Most important is the precise determination of the position of the contact portion, that is the microelectrode body portion devoid of insulation, which is electrically conducting contact with surrounding tissue. It is therefore preferred to for the unique pattern to be disposed in close proximity of the contact section, preferably on an insulated section proximally adjacent to the contact section.

A bundle or array of microelectrodes of the invention comprises three or more microelectrodes, preferably four or more microelectrodes. Each microelectrode comprises at or near its proximal end a means for electric connection to a control unit capable of emitting and/or receiving electrical signals via the microelectrode to or from surrounding tissue. An alternative to forwarding electrical signals arising in the tissue by means of an insulated lead is wireless transmission via an implanted radiofrequency emitter or the like connected with the electrode.

According to a preferred aspect of the invention an electrode body comprises a distal terminal portion provided with a polymer bulge or coat and a portion free of insulation extending between the proximal end of the bulge or coat and the distal end of the first insulation layer.

It is preferred for the unique pattern to extend in a longitudinal direction of the electrode body and to comprise three or more sections separated from each other. To provide good visibility by CT or X-ray it is preferred for the elements of the pattern to be axially disposed in regard of each other at distances of 1 mm or more, in particular of 2 mm or more.

According to another preferred aspect of the invention a number of microelectrodes or most or all microelectrodes of a bundle or array share a pattern with the same number of sections but differing by the distance between the sections.

The body formed by the matrix enclosing a bundle or array of microelectrodes is preferably of cylindrical form and narrowing towards its distal end. The microelectrodes of a bundle or array are preferably disposed in parallel with the cylinder axis, in particular do not deviate from that axis by more than 10% or 15% in a distal direction, i.e. fan out in that direction. To facilitate insertion the matrix body can be provided with a glidant layer, such as a layer of dry gelatin or hyaluronic acid so as to provide a low-friction surface on contact with aqueous body fluid.

A pattern for identification by radiative means disposed on a non-conducting polymer coat of the electrode body is preferably covered by a second non-conducting polymer coat. A pattern comprises three or more separate sections each comprising a metal, such as in form of metal particles dispersed in a polymer or disposed as a metal layer on the first insulation layer. Preferred metals are noble metal such as gold or platinum, copper, chromium, iridium, tungsten, stainless steel.

Individually identifiable microelectrodes of the invention include those with an electrode body of a thickness of 8 μm and more, such as of up to 50 μm or more or of up to 100 μm or even up to 200 μm, in combination with a thickness of the metal layer of 2 μm or more, such as of 5 μm or more or 10 μm or more. It is preferred for the combined thickness of the metal/metal comprising layer and the electrode body or of the metal/metal comprising layer on an insulation layer of the body to exceed the thickness of the electrode body or the combined thickness of the insulation layer and the electrode body by more than 20%, in particular by more than 50%.

Thus, according to the present invention is disclosed a method of identifying, by radiative means, a microelectrode upon its insertion into soft tissue, in particular nervous or endocrine tissue, the microelectrode being comprised by a set of two or more microelectrodes each comprising an electrically conducting electrode body, the microelectrodes being of a design, in particular of same or similar design, that does not allow identification by such means, the method comprising:

providing the microelectrode with a unique pattern of a metal or comprising a metal detectable by computer tomography (CT) or X-ray, the pattern comprising or consisting of three or more sections separated from each other disposed in an axial direction on the microelectrode body and/or on one or more insulating layers on the microelectrode body;

inserting the set of microelectrodes into the tissue simultaneously or consecutively;

identifying the microelectrode by radiative means, in particular CT or X-ray, wherein the unique pattern is disposed near the distal end of the electrode body, in particular within a distance from the distal end comprised by 10% or less, in particular by 5% or less, most preferred by 2% or less, of the electrode body length. According to a preferred aspect of the invention the unique pattern is either not disposed repetitively on the electrode body or, if disposed repetitively, is disposed in a unique number of repetitions on each electrode body of the set.

A microelectrode for use in the method preferably comprises an electrically conducting oblong electrode body; wherein the electrode body is partially covered by a first polymer insulation layer, the unique pattern being disposed on a distal portion of the first insulation layer and covered by a second insulation layer or wherein the unique pattern is disposed on a distal portion of the electrode body and is covered by an insulation layer.

In particular, the unique pattern is disposed near the distal end of the electrode body, that is, within a distance from the distal end comprised by 10% or less, in particular by 5% or less, most preferred by 2% or less, of the electrode body length.

It is furthermore preferred for the unique pattern to not be disposed repetitively on the electrode body or, if disposed repetitively, to be so in a unique number of repetitions on each electrode body of the set.

The method of the invention for simultaneous insertion comprises incorporating the set of two or more microelectrodes into a matrix of a material dissolvable or swellable in aqueous body fluid to form a microelectrode bundle or array; inserting the bundle or the array into soft tissue; upon dissolution or swelling of the matrix material determining the position the unique pattern by radiative means, in particular CT or X-ray.

According to a preferred aspect a method for simultaneous insertion comprises incorporating the set of three or more microelectrodes into a matrix of a material dissolvable or swellable in aqueous body fluid to form a microelectrode bundle or array; inserting the bundle or the array into soft tissue; upon dissolution or swelling of the matrix material determining the position the unique pattern by radiative means, in particular CT or X-ray. The matrix is preferably of cylindrical from narrowing towards its distal end.

A bundle or array for use in the method comprises three or more microelectrodes, more preferred four or more microelectrodes.

According to a further preferred aspect of the invention an electrode body of a microelectrode for use in the method comprises a distal terminal portion provided with a nonconducting polymer coat or bulge and a portion free of insulation extending between the proximal end of the coat or bulge and the distal end of the first insulation layer or the insulation layer. It is preferred for the unique pattern to comprise three or more sections separated from each other. Preferably all microelectrodes of a bundle or array share a pattern with the same number of sections but differ by the distance between the sections.

According to the present invention is also disclosed a microelectrode provided with a unique metallic pattern for identification of the microelectrode by radiative means upon implantation into soft tissue, in particular nervous or endocrine tissue, the microelectrode comprising an oblong electrically conducting body and the pattern comprising three or more sections comprising a metal; wherein the pattern is disposed on a first non-conducting polymer coat of an insulating material covering a proximal portion of the microelectrode body, wherein the pattern comprises three or more sections extending in a longitudinal direction of the electrode body and wherein the sections are covered by a second non-conducting coat of a polymer material; or wherein the pattern is disposed on the electrode body and covered by non-conducting coat of a polymer material; with the proviso that the pattern is disposed near the distal end of the electrode body, that is, within a distance from the distal end of comprised by 10% or less, in particular by 5% or less, most preferred by 2% or less, of the electrode body length.

A section of the unique pattern can be formed by metal particles dispersed in a polymer or by a metal layer. It is preferred for a section to be of annular form and to extend around or substantially around the electrode body. A metal for constituting a section or being comprised by a section of the pattern is preferably selected from the group consisting of noble metal such as gold or platinum, copper, chromium, iridium, tungsten, stainless steel.

The body of the microelectrode is preferably cylindrical. The body has a preferred thickness of from 5 μm or 8 μm to 25 μm or 50 μm and the metal layer has a thickness of from 2 μm or 5 μm to 15 μm or 30 μm. A section of the unique pattern has a preferred axial extension of 1 mm or 2 mm or more.

According to the present invention is also disclosed a bundle or array comprising two or more microelectrodes of the invention, their patterns differing by the distance of their sections in an axial direction. The bundle or array is preferably enclosed by a matrix of a material dissolvable or swellable in aqueous body fluid, in particular one of cylindrical form having a proximal end and a distal end towards which it is narrowing.

According to the present invention is furthermore disclosed the use of the bundle or array of microelectrodes of the invention for implantation into soft tissue, in particular nervous or endocrine tissue.

Each microelectrode of a set of three or more microelectrodes of the invention is provided with a unique pattern capable of being recognized by CT or X-ray. The set can be used for consecutive implantation of its microelectrodes into soft tissue, in particular nervous or endocrine tissue.

A preferred use of the set of three or more microelectrodes of the invention is for determining the position of one or more neurons in soft tissue.

The invention will now be described in greater detail by reference to a preferred embodiment illustrated in a drawing.

DESCRIPTION OF PREFERRED EMBODIMENTS

Example 1

Figure 1:
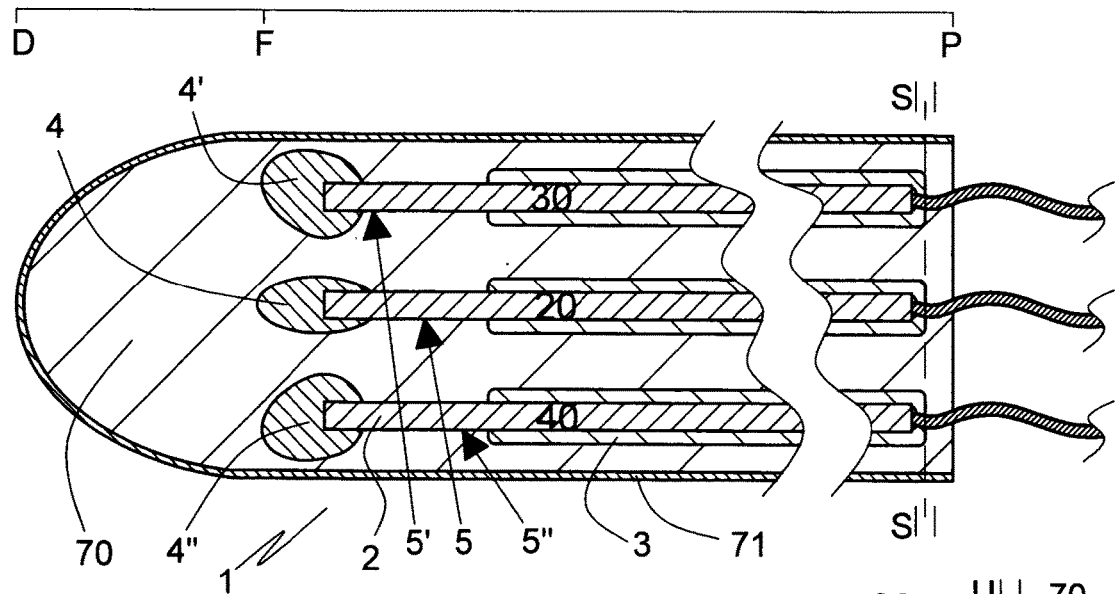
FIGS. 1, 1a illustrates a bundle of five microelectrodes disposed in parallel in a cylindrical matrix of a material which is dissolvable or degradable in aqueous body fluid, in an axial section U-U and a transverse section S-S.
Figure 1A:
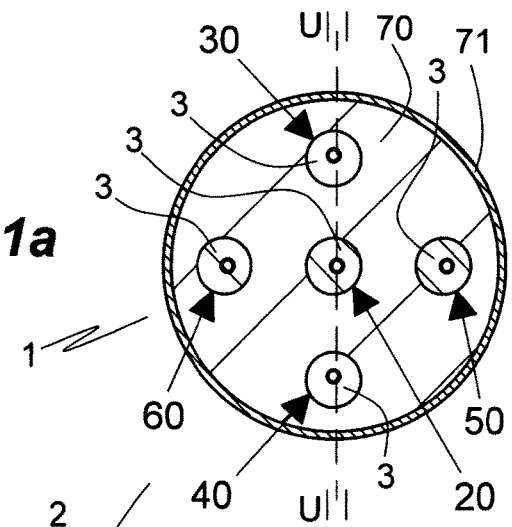
Figure 2A:
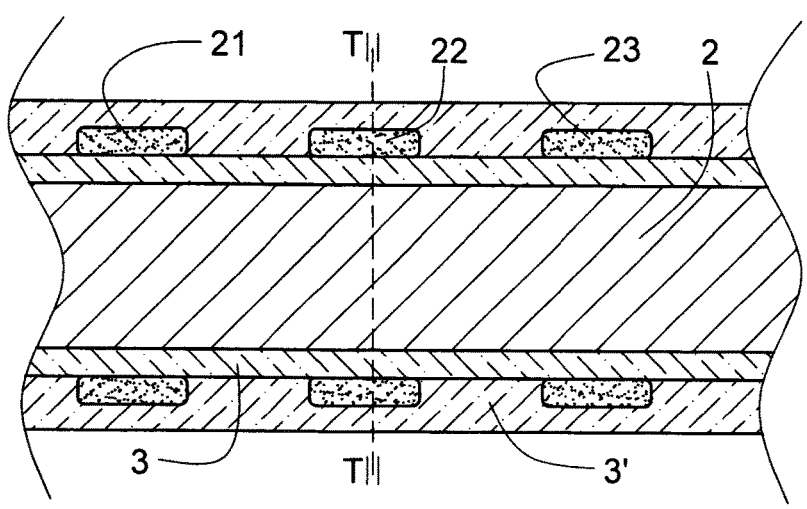
FIG. 2a is an enlarged view of the portion of the microelectrode of FIG. 2 provided with a unique pattern.
Figure 2B:
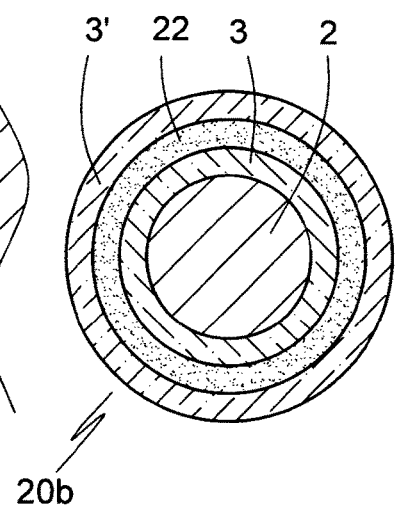
FIG. 2b is correspondingly enlarged view through one of the unique patterns, in a radial section T-T.

The microelectrode bundle 1 of FIGS. 1, 1a comprises five microelectrodes of which four 30, 40, 50, 60 are symmetrically disposed around a central microelectrode 20. At their distal end their metallic or conducting polymer electrode bodies 2 are provided with polymer guide elements of which only those for microelectrodes 20, 30, and 40 are shown. The guide elements are of two kind: a guide element 4 attached to the electrode body 2 of the central microelectrode 20 in a rotationally symmetric manner and four guide elements 4', 4" (the others not shown) attached to the body 2 of the respective microelectrode 30, 40, 50, 60 in a non-rotationally symmetric manner. While the distal terminal portions of the microelectrodes 20, 30, 40, 50, 60 carry a central guide element 4 and peripheral guide elements 4', 4", respectively. The guide elements are electrically insulated by them at those distal terminal portions. Most of the remainder of the microelectrode bodies 2 extending from their proximal ends towards the guide elements 4, 4', 4" is insulated by a polymer coat 3 of, for instance, polyurethane or Parylene C, except for a short non-insulated section 5 extending from the distal end of the coat 3 to the proximal end of the guide elements 4, 4', 4". Upon implantation their non-insulated portions 5, 5', 5" can establish electrical contact with surrounding tissue.

The peripheral microelectrodes 30, 40, 50, 60 have their guide elements 4', 4" disposed in a manner so as to make the guide element axes G-G, G'-G' diverge in a distal direction from their axes H-H, H'-H' and from the axis K- of the central microelectrode 20 extending in parallel and shared by its guide element 4. This disposition of the microelectrodes 20, 30, 40, 50, 60 is stabilized by their embedment in cylindrical matrix 70 of a biocompatible material dissolvable or degradable in aqueous body fluid such as glucose or gelatin. In FIG. 1 the distal and proximal ends of the matrix body are indicated by D and P. The electrodes 20, 30, 40, 50, 60 are arranged in parallel and their distal ends, which are disposed in a common plane, are indicated by F. At its distal end the matrix 70 forms a blunt tip facilitating insertion of the bundle 1 into soft tissue. If the matrix is of a high-friction material or prone to dissolve quickly in aqueous body fluid such as glucose it is advantageously covered by a thin layer 71 of a material delaying dissolution and acting as a glidant, such as gelatin.

Upon insertion of the bundle 1 into soft tissue the matrix 70 starts to dissolve in the body fluid. Upon complete dissolution the electrodes 20, 30, 40, 50, 60 are no longer restrained in their movement in respect of each other. They may be intentionally or unintentionally individually inserted deeper into the tissue so as to occupy a desired position in respect of a target, in particular a neuron or group of neurons. Their initial orientation upon dissolution in combination with the orientation of their guide elements 4, 4', 4" makes the peripheral microelectrodes 30', 40' fan out from the central axis of the K- of the central microelectrode 20, which coincides with the cylinder axis of the electrode bundle 1. Their disposition in living tissue then can only be determined non-invasively, such as by computer tomography (CT) or X-ray. Microelectrodes of the art are however not suitable for identification by these methods, in particular not suitable for identification by CT. To make them detectable by their polymer coat 3 or their guide elements 4, 4', 4" or both they are provided with unique patterns or markers.

In one aspect of the method for marking microelectrodes is provided a polyurethane glue in which sub-micro particles of a noble material such as silver or gold are disposed. Small areas, in particular rings of glue comprising the metal are applied on the polymer coat 3 in a pattern differing for each electrode. While a two-ring pattern can be used, a pattern with three or more rings is preferred. The pattern then is covered by a further layer of non-conducting polymer so as to protect the pattern from contact with tissue or body fluid.

Figure 3:
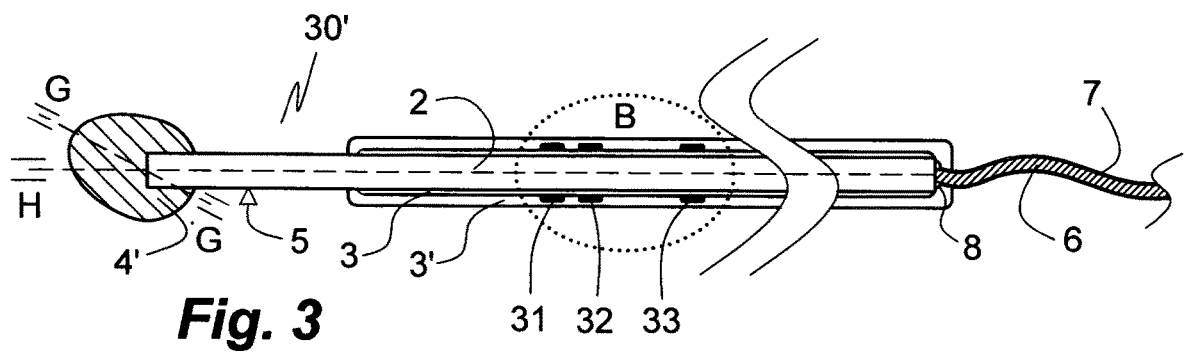
FIGS. 2-4 illustrate three microelectrodes of the bundle of FIG. 1 provided with unique patterns making them discernible in respect of each other by computer tomography (CT), in the same section.
Figure 2:
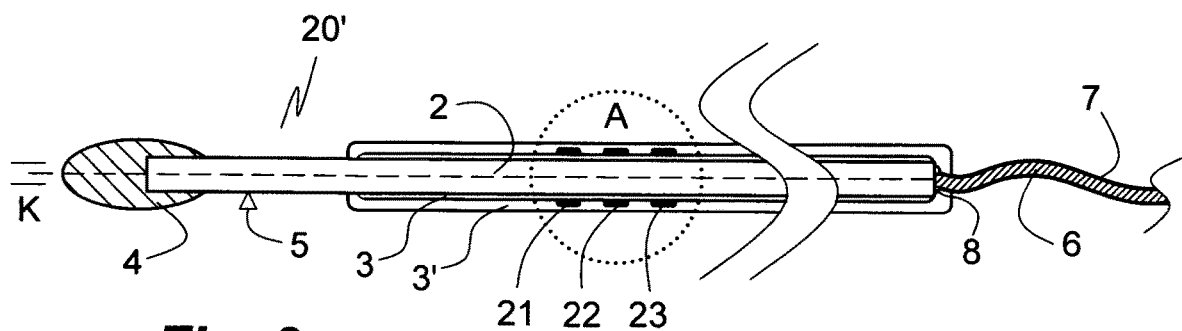
Figure 4:
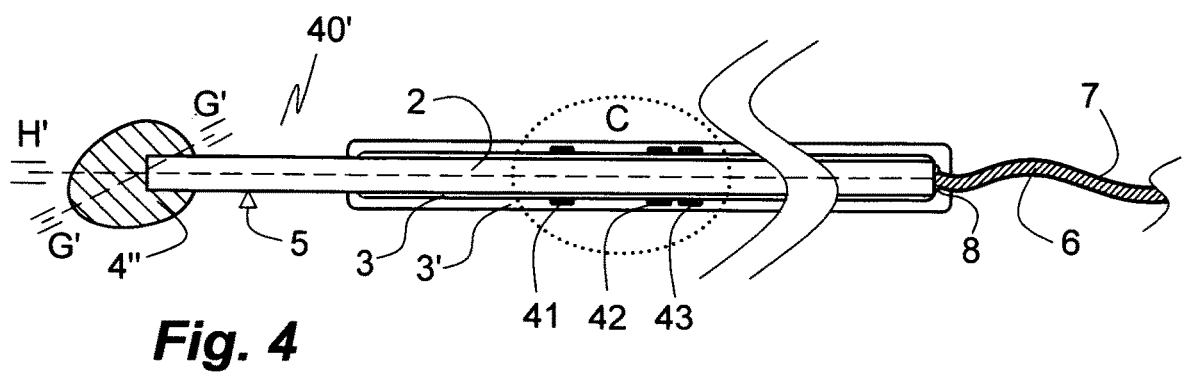

FIGS. 2, 3 and 4 illustrate the electrodes 20', 30', 40' corresponding to non-marked electrodes 20, 30, 40 of FIGS. 1, 1a provided with annular patterns A: 21, 22, 23; B: 31, 32, 33; C: 41, 42, 43, each of which is different by the axial distance between the rings 21, 22, 23; 31, 32, 33; 41, 42, 43 of each pattern A, B, C varying in a manner so as to make each pattern unique. While the distance between neighbouring rings 21, 22; 22, 23; of microelectrode 20' is the same, the distance between rings 31, 32; 33, 34 and between rings 41, 42; 42, 43, respectively, differs in that the distance between the distal and the central ring is smaller in microelectrode 30' whereas it is greater in microelectrode 40'. The opposite is true for distance between the central ring and the proximal ring of these electrodes, the distance between their distal and proximal rings 31, 33; 41, 43 being the same. Other suitable metals for marking of microelectrodes include gold, platinum, iridium but copper, chromium can also be used.

For identification each marked electrode is photographed and the distance between the markings, in particular rings, is determined. The CT software is calibrated to allow automatic identification of each microelectrode.

In another aspect of the method for marking microelectrodes with metal patches or rings a metal beam is sprayed on an insulated portion of the electrode body through slits of a mask, then covered with a layer of non-conducting polymer. Another useful method comprises ion sputtering through a mask.

Microelectrodes presently used in the method have a preferred diameter of about 12 μm including the insulation layer of about 2 μm. A layer of metallic marker of 3 μm thickness disposed on the insulation layer results in a total useful diameter of about 18 μm, well above the CT detection limit, disregarding from the additional insulation layer deposed on the metallic marker layer which does not add detectability.

Example 2

Figure 5:
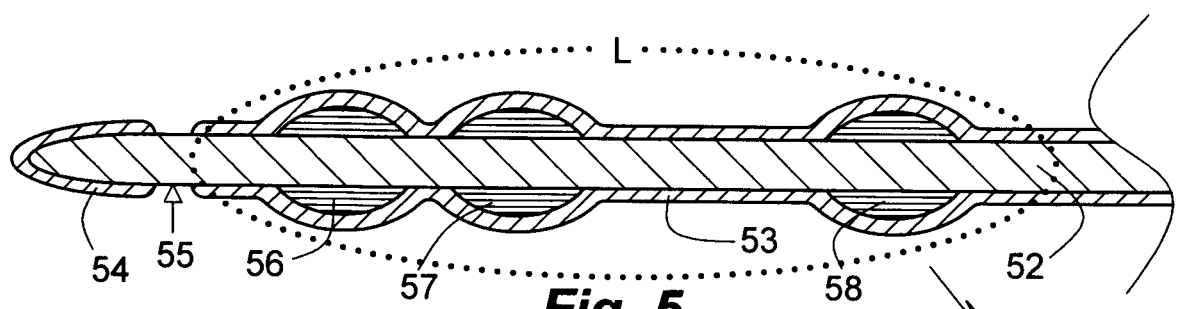
FIGS. 5-8 illustrate further embodiments of a microelectrode of the invention, in an axial section corresponding to that of FIG. 2.
Figure 6:
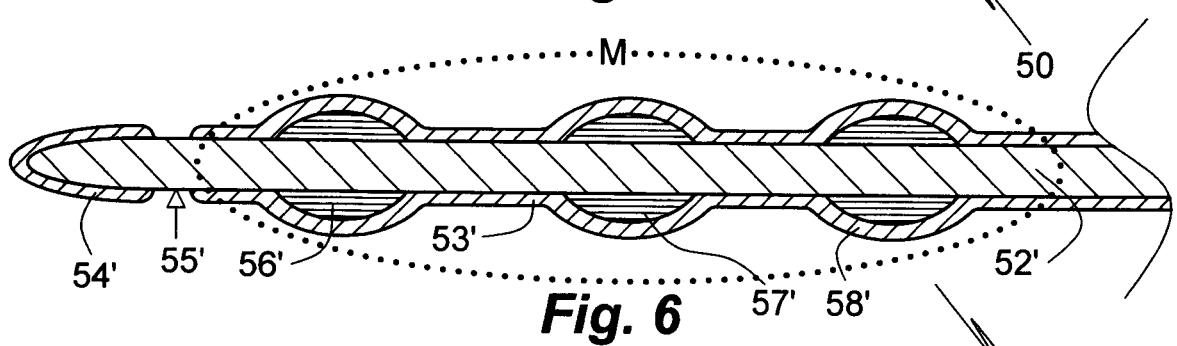
Figure 7:
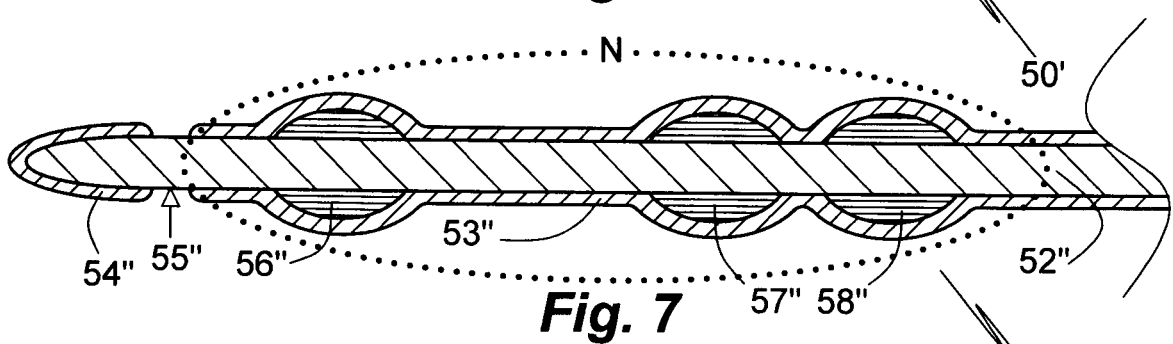

FIGS. 5-7 illustrate a set of three microelectrodes 50, 50', 50" provided with unique patterns L, M, N, each comprising three axially disposed metallic elements or elements comprising a metal 56, 57, 58; 56', 57', 58'; 56", 57", 58" on the electrode body 53, 53', 53". The proximal portion of the electrode body 52, 52', 52" and the metallic elements 56, 57, 58; 56', 57', 58'; 56", 57", 58" disposed thereon is covered by a main insulation polymer layer 53, 53', 53", which extends to near the distal end of the electrode body 52, 52', 52". The tip of the distal end is covered by a terminal insulation layer 54, 54', 54". A short portion of the electrode body 55, 55', 55" extending between the proximal end of the terminal insulation layer 54, 54', 54" and the distal end of the main insulation layer 53, 53', 53" is naked and in electrical contact with surrounding tissue upon dissolution or degradation of the matrix (not shown) of the electrode bundle in which the microelectrodes 50, 50', 50" are embedded.

Example 3

Figure 8:
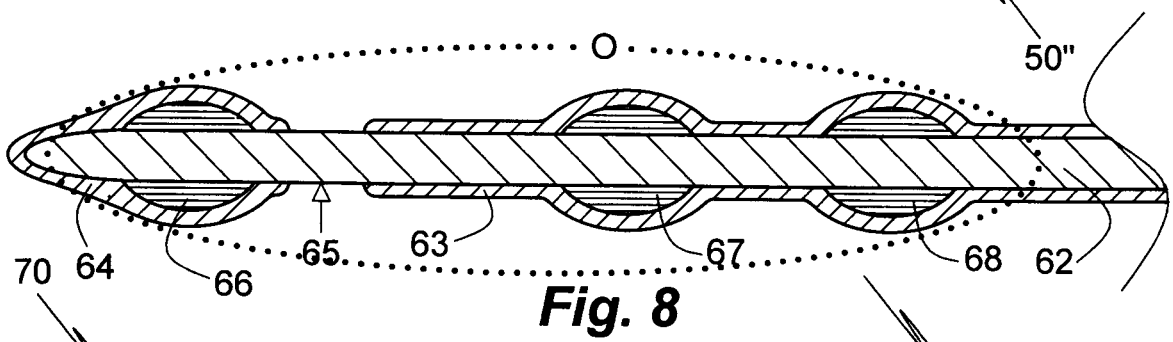

FIG. 8 shows a first variety 60 of the microelectrode 50, 50', 50" of FIGS. 5 to 7, from which it differs by one metallic element or segment 66 of the unique pattern O being disposed at the distal tip of the electrode body 62 insulated by an insulating polymer coat 64 corresponding to the terminal insulation layer 54, 54', 54" of the embodiment of FIGS. 5 to 7. The most distally disposed segment 66 of the pattern O is covered by an insulation layer 64 separate from the main insulation layer 63 covering the two other metallic segments 67, 68, the naked portion 65 of the electrode body 62 extending between them.

Example 4

Figure 9:
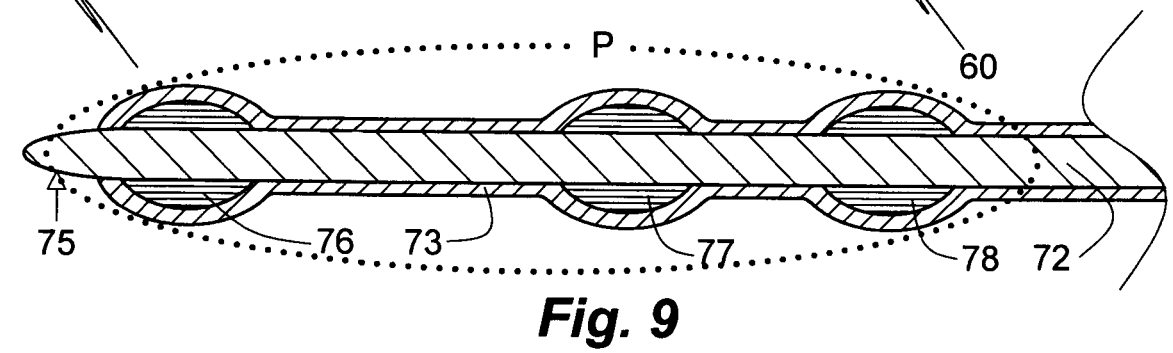

FIG. 9 shows a second variety 70 of the microelectrode 50, 50', 50" of FIGS. 5 to 7, from which it differs comprising a single insulation layer 73 covering the unique pattern P comprising three metallic segments 76, 77, 78 attached to the electrode body 72. The naked portion 75 of the microelectrode 70 extends from the distal end of the layer 73 to the distal tip of the electrode 70.

The invention claimed is:

1. A method of identifying, by a radiative means, at least one microelectrode within a set of two or more microelectrodes insertable in soft tissue, the at least one microelectrode comprising an electrically conducting electrode body with a distal end and a distal section that is configured to make electrical contact with the soft tissue, and a unique pattern of three or more sections, each section comprising a metal detectable by radiative means, the three or more sections being separated from each other and disposed along an axial direction on the at least one microelectrode within a distance from the distal end of the electrode body that is 10% or less of the electrode body's length;

wherein the sections of the unique pattern are disposed on a first non-conducting coat of polymer material covering a portion of the electrode body, and the sections of the unique pattern are covered by a second coat of non-conducting polymer material; or wherein the sections of the unique pattern are disposed on a portion of the electrode body and covered by a non-conducting coat of a polymer material, the method comprising:

inserting the set of microelectrodes into the tissue simultaneously or consecutively; and identifying the at least one microelectrode by the radiative means.

2. The method of claim 1, wherein the radiative means is either computer tomography (CT) or X-ray.

3. The method of claim 1, wherein the unique pattern is either not disposed repetitively on the at least one microelectrode or, if disposed repetitively, is disposed in a unique number of repetitions on each microelectrode of the set of two or more microelectrodes.

4. The method of claim 3, wherein the unique pattern is disposed on the first non-conductive coat of polymer material and covered by the second non-conductive coat of polymer material.

5. The method of claim 1, comprising:

incorporating the set of two or more microelectrodes into a matrix of a material dissolvable or swellable in aqueous body fluid to form a microelectrode bundle or array;

inserting the bundle or the array into soft tissue;

upon dissolution or swelling of the matrix material determining the unique pattern of the at least one microelectrode by the radiative means.

6. The method of claim 5, wherein the bundle or array comprises three or more microelectrodes.

7. The method of claim 6, wherein all microelectrodes of the bundle or array share a pattern with the same number of sections but differ by the distance between the sections.

8. The method of claim 5, wherein the matrix comprises a cylindrical portion and a portion that narrows from the cylindrical portion to the matrix's distal end.

9. The method of claim 1, further comprising a non-conducting polymer coat or bulge at the distal end of the electrode body separated from the first insulation layer by a portion free of insulation extending between the proximal end of the non-conducting polymer coat or bulge and the first non-conducting coat of polymer.

10. A microelectrode provided with a unique pattern that is insulated and configured for identification of the microelectrode by radiative means while the microelectrode is implanted in soft tissue, the microelectrode comprising an oblong electrically conducting electrode body having a tissue contacting distal section that makes electrical contact with the soft tissue while the microelectrode is implanted in the soft tissue, extends from a distal end of the microelectrode or is disposed in proximity of the distal end of the microelectrode, the unique pattern comprising three or more separated sections, each section comprising a metal and extending in a longitudinal direction of the electrode body;

wherein the unique pattern is disposed within a distance from the distal end that is 10% or less of the electrode body's length; and wherein the sections of the unique pattern are disposed on a first non-conducting coat of polymer material covering a portion of the electrode body, and the sections of the unique pattern are covered by a second coat of non-conducting polymer material; or wherein the sections of the unique pattern are disposed on a portion of the electrode body and covered by a non-conducting coat of a polymer material.

11. The microelectrode of claim 10, wherein each section is formed by metal particles dispersed in a polymer material.

12. The microelectrode of claim 11, wherein each section is of annular form extending around the electrode body.

13. The microelectrode of claim 10, wherein each section is formed by a metal layer.

14. The microelectrode of claim 10, wherein the metal is selected from the group consisting of noble metal, copper, chromium, iridium, tungsten, stainless steel.

15. The microelectrode of claim 10, wherein the electrode body is cylindrical.

16. The microelectrode of claim 10, wherein the electrode body has a thickness of from 5 µm to 50 µm and the metal layer has a thickness of from 2 µm to 30 µm.

17. The microelectrode of claim 10, wherein each section has an axial extension of 1 mm or 2 mm or more.

18. A bundle or array comprising two or more microelectrodes of claim 10, wherein the patterns differ by the distance of their sections in an axial direction.

19. The bundle or array of claim 18, wherein the two or more microelectrodes are in into a matrix of a material dissolvable or swellable in aqueous body fluid.

20. The bundle or array of claim 19, wherein the matrix comprises a proximal end, a distal end, a cylindrical portion, and a portion that narrows from the cylindrical portion to the distal end.

21. A set of three or more microelectrodes of claim 10, wherein each microelectrode is provided with a unique pattern capable of being recognized by CT or X-ray.

* * * * *